US012653985B2

(12) United States Patent
Rehberger

(10) Patent No.: US 12,653,985 B2
(45) Date of Patent: Jun. 16, 2026

(54) CATHETER DEVICE COMPRISING A SENSOR DEVICE FOR MEASURING A FORCE EFFECT

(71) Applicant: VascoMed GmbH, Binzen (DE)

(72) Inventor: Frank Rehberger, Freiburg (DE)

(73) Assignee: VascoMed GmbH, Binzen (DE)

( * ) Notice: Subject to any disclaimer, the term of this patent is extended or adjusted under 35 U.S.C. 154(b) by 582 days.

(21) Appl. No.: 18/245,948

(22) PCT Filed: Aug. 13, 2021

(86) PCT No.: PCT/EP2021/072586
§ 371 (c)(1),
(2) Date: Mar. 20, 2023

(87) PCT Pub. No.: WO2022/063486
PCT Pub. Date: Mar. 31, 2022

(65) Prior Publication Data
US 2023/0381451 A1     Nov. 30, 2023

(30) Foreign Application Priority Data

Sep. 23, 2020    (EP) .................................... 20197778

(51) Int. Cl.
*A61M 25/00*        (2006.01)
(52) U.S. Cl.
CPC ... *A61M 25/0043* (2013.01); *A61M 2205/332* (2013.01)
(58) Field of Classification Search
CPC ........ A61M 20/0067; A61M 2205/332; A61B 2090/065; A61B 5/6885; G01L 1/246
See application file for complete search history.

(56) References Cited

U.S. PATENT DOCUMENTS

| | | | |
|---|---|---|---|
| 9,689,759 B2 * | 6/2017 | Fandrey | ............. A61B 18/1492 |
| 2006/0200049 A1 | 9/2006 | Leo et al. | |
| 2012/0220879 A1 | 8/2012 | Fandrey et al. | |
| 2014/0081264 A1 | 3/2014 | Fandrey et al. | |

OTHER PUBLICATIONS

International Search Report (PCT/ISA/210) and Written Opinion (PCT/ISA/237) mailed on Jan. 10, 2022, by the European Patent Office as the International Searching Authority for International Application No. PCT/EP2021/072586. (15 pages).

* cited by examiner

*Primary Examiner* — Laura A Bouchelle
(74) *Attorney, Agent, or Firm* — Buchanan Ingersoll & Rooney PC

(57)                    ABSTRACT

A catheter device comprises a measuring device for measuring a force effect on the catheter device. The measuring device comprises a force transducer comprising a plurality of transducer sections and an optical fiber arranged on the force transducer, wherein the transducer sections form at least a pair of adjacent transducer sections which are connected to one another by means of a connecting section and which can be moved relative to one another with deformation of the connecting section, and wherein the optical fiber comprises at least one sensor device for measuring a force effect between the transducer sections of the at least one pair of adjacent transducer sections. The at least one sensor device comprises a first optical grating and a second optical grating for measuring a force effect between the transducer sections of the at least one pair of adjacent transducer sections.

14 Claims, 6 Drawing Sheets

CATHETER DEVICE COMPRISING A SENSOR DEVICE FOR MEASURING A FORCE EFFECT

CROSS-REFERENCE TO RELATED APPLICATIONS

This application is the United States National Phase under 35 U.S.C. § 371 of PCT International Patent Application No. PCT/EP2021/072586, filed on Aug. 13, 2021, which claims the benefit of European Patent Application No. 20197778.2, filed on Sep. 23, 2020, the disclosures of which are hereby incorporated by reference herein in their entireties.

TECHNICAL FIELD

The present invention relates to a catheter device according to the preamble of claim 1 and a force transducer provided particularly for use in the catheter device according to the present invention.

BACKGROUND

Such a catheter device comprises a measuring device for measuring a force effect on the catheter device. The measuring device comprises a force transducer comprising a plurality of transducer sections and an optical fiber arranged on the force transducer. The transducer sections form at least one pair of adjacent transducer sections connected to one another by means of a connecting section and movable with respect to one another with deformation of the connecting section. The optical fiber comprises at least one sensor device for measuring a force effect between the transducer sections of the at least one pair of adjacent transducer sections.

Such a catheter device can be configured as an ablation catheter, for example. Cardiac arrhythmias can be treated by means of an ablation catheter by selectively switching off heart tissue, for example, by heating, in order to locally suppress the generation or conduction of electrical impulses. For this purpose, an electrode can be brought into contact with heart tissue, for example, in order to locally heat tissue and thus destroy it by introducing a high-frequency current as part of so-called high-frequency ablation. The catheter device can, however, also be configured as a diagnostic catheter or as an insertion catheter.

In such a catheter device, a force effect should be reliably determined in order to determine whether there is contact between the catheter device and the tissue to be treated and with what force the catheter device acts on the tissue.

In a catheter device known from U.S. Publication No. 2014/0081264 A1, an optical fiber is arranged on a force transducer, which optical fiber comprises a plurality of sensor devices, each comprising an optical grating. A force effect between transducer sections of the force transducer is intended to be measured by means of the sensor devices, wherein the force transducer is designed in such a way that each sensor device can measure a force effect along a defined spatial direction.

In a catheter device known from U.S. Publication No. 2006/0200049 A1, different optical fibers are arranged on a body, each optical fiber comprising a sensor device. A force effect can be measured by means of the sensor devices, wherein sensor devices are able to comprise, for example, optical gratings in the form of fiber Bragg gratings.

The present disclosure is directed toward overcoming one or more of the above-mentioned problems, though not necessarily limited to embodiments that do.

SUMMARY

An object of the present invention is to provide a catheter device which enables a reliable and precise measurement of a force effect on the catheter device.

At least this object is achieved by a catheter device and a force transducer having the features set forth in the claims.

According to claim 1, the catheter device according to the present invention comprises at least one sensor device, a first optical grating and a second optical grating for measuring a force effect between the transducer sections of the at least one pair of adjacent transducer sections.

In the measuring device of the catheter device, a measurement of a force effect takes place between transducer sections, each of which is connected to one another in pairs by means of a connecting section and can be moved with respect to one another in a predetermined manner by means of the connecting section. The transducer sections can particularly, for example, be pivotable with respect to one another or axially adjustable with respect to one another, so that a force effect along a predefined spatial direction can be determined on the basis of a movement of two transducer sections with respect to one another.

The force effect is measured here by means of one or more sensor devices that are formed on an optical fiber. Here, a sensor device is advantageously associated with each pair of adjacent transducer sections, wherein each sensor device comprises a first optical grating and a second optical grating, which are used together to measure a force effect between the transducer sections of the respective pair of adjacent transducer sections.

Measurement accuracy for measurement between the two adjacent transducer sections can be improved by using two optical gratings of an optical fiber for measuring a force effect in a region between the two adjacent transducer sections. The optical gratings can be configured here in the same way and interact in order to enable a measurement and evaluation on the basis of an optical signal obtained by the two optical gratings. In this case, for example, temperature compensation can be carried out in order, for example, in an ablation catheter, to take into account the effect of a temperature change on a measurement and thus to determine a force effect that is not influenced by temperature. The optical gratings can, however, also be configured differently and enable separate measurement and evaluation, wherein the measurement accuracy can be improved, for example, by averaging.

Furthermore, a plurality of optical fibers can be arranged on the force transducer. In one embodiment, the catheter device according to the present invention comprises two to four optical fibers, preferably two or three.

In one embodiment, the transducer sections of the force transducer are lined up along a longitudinal axis. The longitudinal axis of the force transducer here advantageously corresponds to the longitudinal axis of the catheter device, so that the transducer sections adjoin one another longitudinally on the catheter device, wherein transducer sections that are adjacent in pairs are connected to one another by means of a connecting section that can be deformed in a defined manner.

The transducer sections can be moved with respect to one another in different ways through the connecting sections, so that a specific force effect can be measured along a defined direction by means of each sensor device associated with a pair of transducer sections. A force acting on the catheter device is thus broken down into vector components by the force transducer, wherein it is possible for these vector components to be measured by different sensor devices.

In one embodiment, the connecting section comprises, for example, at least one pair of adjacent transducer sections connected to one another by means of a connecting section movable about a defined spatial direction extending transversely to the longitudinal axis. By specifying the connecting section, the transducer sections can thus be moved with respect to one another in the spatial direction defined by the connecting section, so that a force effect about the respective spatial direction can be determined on the basis of a force measurement by a sensor device associated with the respective pair of transducer sections.

The transducer sections of a pair of adjacent transducer sections can here essentially only be moved about the defined spatial direction so that a deflection at the transducer sections transversely to the longitudinal axis and transversely to the defined spatial direction can be measured using the sensor device.

In this case, the connecting section can be configured, for example, as a web extending between the associated, adjacent transducer sections, which web can be moved in a flexible manner essentially exclusively about the associated, defined spatial direction.

In an advantageous embodiment, at least two pairs of adjacent transducer sections can be present, each of which is connected to one another by means of a connecting section, wherein the connecting sections are movable in different defined spatial directions extending transversely to the longitudinal axis and thus provide mobility of the transducer sections about different spatial directions. The different spatial directions can, for example, be directed perpendicular to one another and thus span a plane of motion perpendicular to the longitudinal axis of the force transducer, so that a force effect in the plane of motion extending perpendicular to the longitudinal axis can be determined by means of the sensor devices associated with the pairs of transducer sections.

In a further advantageous embodiment, more than two pairs of adjacent transducer sections can also be provided, each of which can be moved about different spatial directions. Two spatial directions can enclose, for example, an angle of 90° with respect to one another in a plane perpendicular to the longitudinal axis, while a third spatial direction is arranged at an angle of 45° to the other two spatial directions. In this way, measurement accuracy can be improved by performing an additional force measurement on a third pair of transducer sections.

In addition or as an alternative to the pairs of adjacent transducer sections for measuring a force effect in a plane perpendicular to the longitudinal axis, a pair of adjacent transducer sections can be provided, which are connected to one another by means of a connecting section and can be moved axially along the longitudinal axis relative to one another with axial deformation of the connecting section. In this case, the connecting section can be configured, for example, as an axially resilient spring section, thus enabling an axial adjustment of the adjacent transducer sections with respect to one another. Axial movement and deflection of the transducer sections with respect to one another can thus be detected and measured by means of an associated sensor device, so that an axial force effect can be determined.

In one embodiment, the catheter device comprises an inner tubular element arranged radially inside the force transducer, thus forming a first support section and a second support section. The first support section is connected to a transducer section of a pair of adjacent transducer sections and the second support section is connected to the respective other transducer section of the pair of adjacent transducer sections in such a way that when the transducer sections are moved axially with respect to one another, the support sections are also moved axially with respect to one another and thus adjusted together with the transducer sections.

Here, an axially resilient spring section is advantageously arranged between the support sections, so that the support sections are supported axially resiliently with respect to one another.

The axially resilient spring section between the support sections is provided in addition to the connecting section between the transducer sections. The transducer sections are thus connected to one another by means of the associated connecting section and are additionally supported with respect to one another by means of the support sections of the inner tubular element and the axially resilient spring section arranged between the support sections. Such a configuration of the inner tubular element enables a simplified manufacture of the catheter device, if necessary, because the inner tubular element serving as a carrier for the force transducer and the force transducer can be manufactured with increased tolerances, while the force transducer is reliably supported and, particularly, held torsionally stable by means of the support sections of the inner tubular element. The transducer section of the force transducer and the axially resilient section of the inner tube can particularly be offset from one another along the above-mentioned longitudinal axis in such a way that the inner tube supports the transducer section of the force transducer and a support section of the force transducer supports the axially resilient section of the inner tube against bending.

In one embodiment, the optical fiber extends along the longitudinal axis on the force transducer. The optical fiber here is fixedly connected to the force transducer at least at defined fastening regions, particularly in the region of the transducer sections, so that a deflection of transducer sections with respect to one another leads to a change in length, particularly an elongation, on the optical fiber and can thus be measured by means of the optical grating of the optical fiber.

In general, a change in length, particularly an elongation on the optical fiber, leads to a change in the optical properties of the optical gratings, particularly a change in the grating spacing and in the distance between the optical gratings with respect to one another. The optical gratings here can be spaced a nominal distance from one another along the longitudinal axis, wherein the distance is changeable during a movement between transducer sections of an associated pair of adjacent transducer sections, which can be recognized and determined on the basis of an evaluation of optical signals. Conclusions can be drawn here about a force effect on the force transducer and thus on the catheter device from the change in length on the optical fiber, wherein the force effect can be determined, for example, by means of calibration, within the framework of which a deflection on the force transducer and an accompanying deformation, particularly elongation on the optical fiber, is related to a force effect on the force transducer.

The optical gratings of each sensor device can be configured in the same way or differently.

For example, the optical gratings of a sensor device can each be configured as a fiber Bragg grating. A fiber Bragg grating (FBG for short) is an optical interference filter written into the optical fiber, which optical interference filter is formed by a periodic modification of the refractive index of the optical fiber. Layers of a first refractive index alternate periodically with layers of a second refractive index, so that a periodic arrangement in the manner of a grating is created. A fiber Bragg grating has a center wavelength at which a comparatively narrow-band reflection signal is obtained. A fiber Bragg grating usually has a comparatively small grating period of less than 1 μm, that is, in the nanometer range.

The fiber Bragg gratings can be configured identically or differently. Identical fiber Bragg gratings have the same center wavelength, while different fiber Bragg gratings can differ in their center wavelength.

Identical fiber Bragg gratings preferably form an optical resonator in the form of a Fabry-Perot interferometer, in which transmission occurs when a resonance condition is met and a narrow-band valley occurs accordingly in a reflection spectrum at a resonant wavelength.

When using similar fiber Bragg gratings to form a Fabry-Perot interferometer, a force effect can be differentiated from a temperature influence in order to measure a force effect while calculating and compensating for a temperature influence. This is done by evaluating information obtained, on the one hand, using the spectrum obtained for a fiber Bragg grating and, on the other hand, using the spectrum of the Fabry-Perot interferometer.

If the fiber Bragg gratings are configured differently, that is, if they have a different center wavelength, at least averaging is possible based on signals obtained at the different gratings, so that the accuracy and reliability of the force measurement can be improved in this way.

In one embodiment, one of the optical gratings can be configured as a fiber Bragg grating and the other of the gratings as a so-called long-period grating (LPG for short). In a long-period grating, the optical fiber has a periodic modification of the refractive index with a comparatively large grating period, for example, in a range between 0.1-1 mm.

Even when using a combination of a fiber Bragg grating and a long-period grating, compensation for a temperature change is possible, so that a force effect can be differentiated from the influence of a temperature change and thus a force effect can be determined while compensating for a temperature influence.

In one embodiment, the catheter device comprises an evaluation device configured to evaluate an optical signal for determining a force effect on the force transducer. The optical signal is received as a response signal to a fed-in optical signal and can particularly be present as a reflection signal that has been reflected on the optical gratings of each sensor device. The optical signal can be evaluated in order to determine a force effect on the force transducer on the basis of the optical signal, particularly on the basis of a change in the optical signal compared to a defined, unloaded initial state of the force transducer.

The sensor devices, which each comprise two optical gratings and are used to determine a force effect on different pairs of transducer sections, can be arranged on a single optical fiber. An evaluation can be carried out here on the basis of a single, particularly broadband, fed-in optical signal, wherein the optical gratings of the different sensor devices differ in their optical properties and reflect particularly in the range of different wavelengths. Optical signals that are received from different sensor devices thus differ in wavelength and can be differentiated and evaluated accordingly in order to evaluate information from the individual sensor devices and thus to determine a force effect in the region of the different sensor devices and thus along the different force directions associated with the different sensor devices.

In one embodiment, the evaluation device can particularly be configured to evaluate a change in wavelength of the optical signal in order to determine the force effect. In the event of a force effect on the force transducer and an accompanying deflection of two transducer sections with respect to one another, there is a change in length on the optical fiber in the region of the sensor device associated with the transducer sections, particularly an elongation on the optical fiber and thus a change in the optical properties of the optical grating of the sensor device. Particularly, a grating period of the optical gratings and the distance between the optical gratings can also change, which leads to a change in the optical signal obtained and which can be evaluated accordingly.

If the optical gratings are, for example, two fiber Bragg gratings which together form a Fabry-Perot interferometer, the result is, for example, a shift in the spectrum of the individual fiber Bragg gratings and also a shift in the resonance spectrum of the Fabry-Perot interferometer. Information obtained from this can be evaluated in order to differentiate a change in length as a result of a force effect on the force transducer and a change in length due to a change in temperature and thus to determine the force effect while compensating for temperature influences.

If the optical gratings are, on the one hand, a fiber Bragg grating and, on the other hand, a long-period grating, different information is obtained from the different gratings, which in turn can be evaluated in order to differentiate a change in length as a result of a force effect on the force transducer and a change in length as a result of a change in temperature and thus to determine the force effect while compensating for temperature influences.

A force transducer is provided which is configured particularly for use in a catheter device or one of the associated embodiments and is provided for this purpose. The force transducer comprises a plurality of transducer sections, wherein the transducer sections form at least one pair of adjacent transducer sections connected to one another by means of a connecting section and can be moved with respect to one another with deformation of the connecting section, and the plurality of transducer sections are lined up along a longitudinal axis.

According to the present invention, it is particularly provided that the connecting section of at least one pair of adjacent transducer sections is axially deformable along the longitudinal axis in such a way that the transducer sections of the at least one pair of adjacent transducer sections can be moved axially along the longitudinal axis with respect to one another by means of the connecting section.

The connecting section is preferably formed by an axially resilient spring section.

In one embodiment, an inner tubular element is provided which is arranged radially inside the force transducer, the inner tubular element comprising a first support section connected to a transducer section of the at least one pair of adjacent transducer sections and a second support section connected to the other transducer section of the at least one pair of adjacent transducer sections, wherein the first support section and the second support section are connected to one another by means of an axially resilient spring section. The transducer section of the force transducer and the axially resilient section of the inner tube are here preferably offset from one another along the axis so that the inner tube supports the transducer section of the force transducer and a support section of the force transducer supports the axially resilient section of the inner tube against bending.

Particularly, a catheter device is furthermore provided according to the present invention, which catheter device comprises the force transducer, and preferably an inner tubular element according to the previous paragraph arranged radially inside the force transducer.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

An idea on which the present invention is based will be explained in more detail below with reference to the embodiments shown in the figures. Shown are.

DETAILED DESCRIPTION

Figure 1:
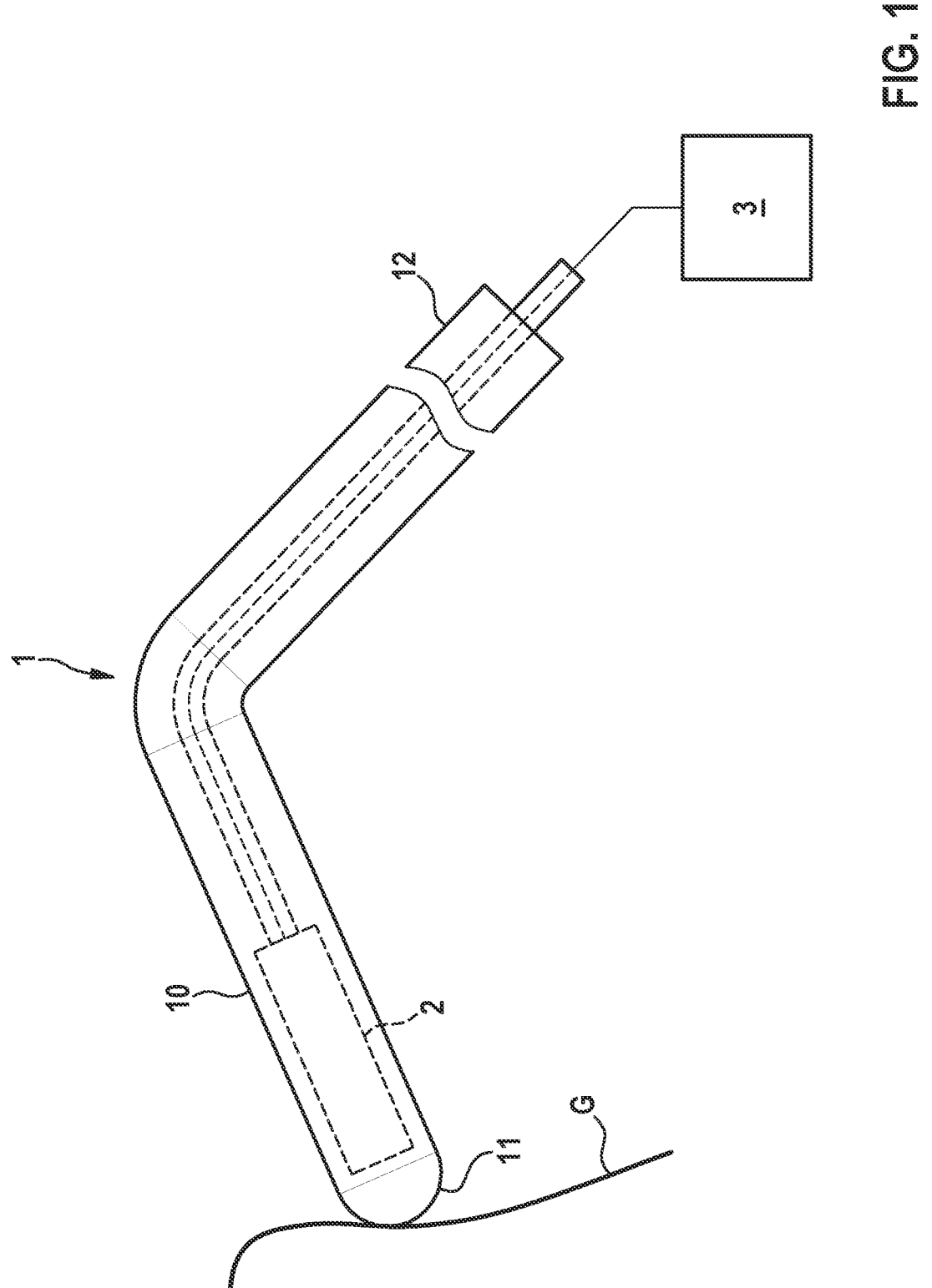
FIG. 1 a schematic view of a catheter device comprising a measuring device.

FIG. 1 shows a schematic view of a catheter device 1 which can, for example, actualize an ablation catheter.

The catheter device 1 comprises a tubular body 10 which can be introduced into the patient's body and a proximal end 12 remaining outside the patient's body and, at a distal end facing away from the proximal end 12, an electrode 11 for contact with and action on tissue G within the patient.

The electrode 11 is used, for example, to introduce a high-frequency current into tissue G as part of an ablation, in order in this way to effect local heating of the tissue G and thereby switching off the tissue G, that is, suppressing stimuli locally on the tissue G.

At the distal end, the catheter device 1 comprises a measuring device 2 for determining a force effect on the catheter device 1 in order to be able to determine, particularly during an ablation, whether the catheter device 1 is in contact with tissue G and with what force the catheter device 1 applies to the tissue G here.

Figures 2, 3:
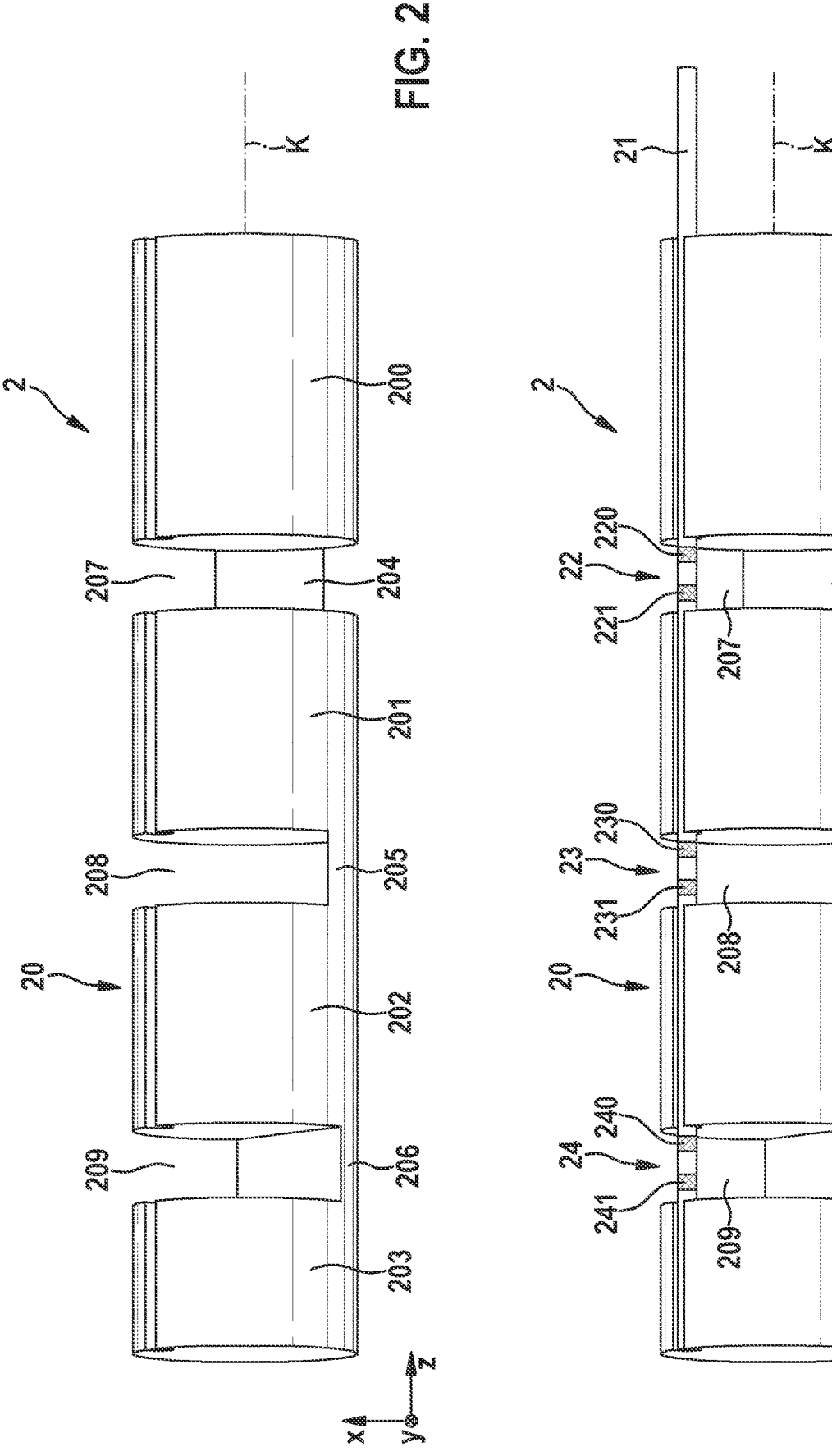
FIG. 2 a view of an embodiment of a force transducer of the measuring device.
FIG. 3 a view of the force transducer, comprising an optical fiber arranged thereon and sensor devices configured in the region of transducer sections.

The measuring device 2 comprises a force transducer 20, depicted in an embodiment in FIG. 2, which comprises transducer sections 200-203 lined up axially along a longitudinal axis K, each of which is connected to one another in pairs by means of connecting sections 204-206.

As can be seen from FIG. 3, an optical fiber 21, which forms sensor devices 22, 23, 24, is arranged on the force transducer 20.

Adjacent transducer sections 200-203 are each separated from one another by means of a recess 207-209 which is bridged by the respectively associated connecting section 204-206 and are therefore movable in pairs with respect to one another in the region of the recesses 207-209. The connecting sections 204-206 are configured in the manner of webs and extend axially along the longitudinal axis K between the respectively associated transducer sections 200-203, wherein the connecting sections 204-206 are shaped in such a way that two adjacent transducer sections 200-203 can each be moved, in particular pivoted, about an associated, defined spatial direction X, Y, Z with respect to one another.

In the embodiment of the force transducer 20 according to FIGS. 2 and 3, transducer sections 200, 201 form a first pair of adjacent transducer sections which are connected to one another by means of a connecting section 204 and can be pivoted with respect to one another essentially about the spatial direction X by means of the connecting section 204.

In contrast, the transducer sections 201, 202 form a pair of adjacent transducer sections which can be pivoted with respect to one another by means of the associated connecting section 205 essentially about the spatial direction Y perpendicular to the spatial direction X.

In contrast, the transducer sections 202, 203 are connected to one another by means of a connecting section 206 which is extended at an angle of 45° to the spatial direction X and to the spatial direction Y (in a plane spanned by the spatial directions X, Y and perpendicular to the longitudinal axis K) between the associated transducer sections 202, 203, so that the transducer sections 202, 203 can be moved with respect to one another about a spatial direction extending at an angle of 45° to the spatial direction X and to the spatial direction Y.

A force effect can thus be determined at the sensor devices 22, 23, 24, which force effect is directed perpendicular to the respective spatial direction (which indicates the bending axis for the associated connecting section 204-206) and the longitudinal axis K.

A sensor device 22, 23, 24 is associated with each pair of transducer sections 200-203 in order to measure a movement between the respectively associated transducer sections 200-203. The sensor devices 22, 23, 24 here are each arranged in the region of the recess 207-209 on the optical fiber 21 bridging the recesses 207-209, are spaced radially from the connecting sections 204-206 and can thus absorb a deformation on the optical fiber 21 as a result of a movement of the respective transducer sections 200-203 with respect to one another.

Figures 4A, 4B:
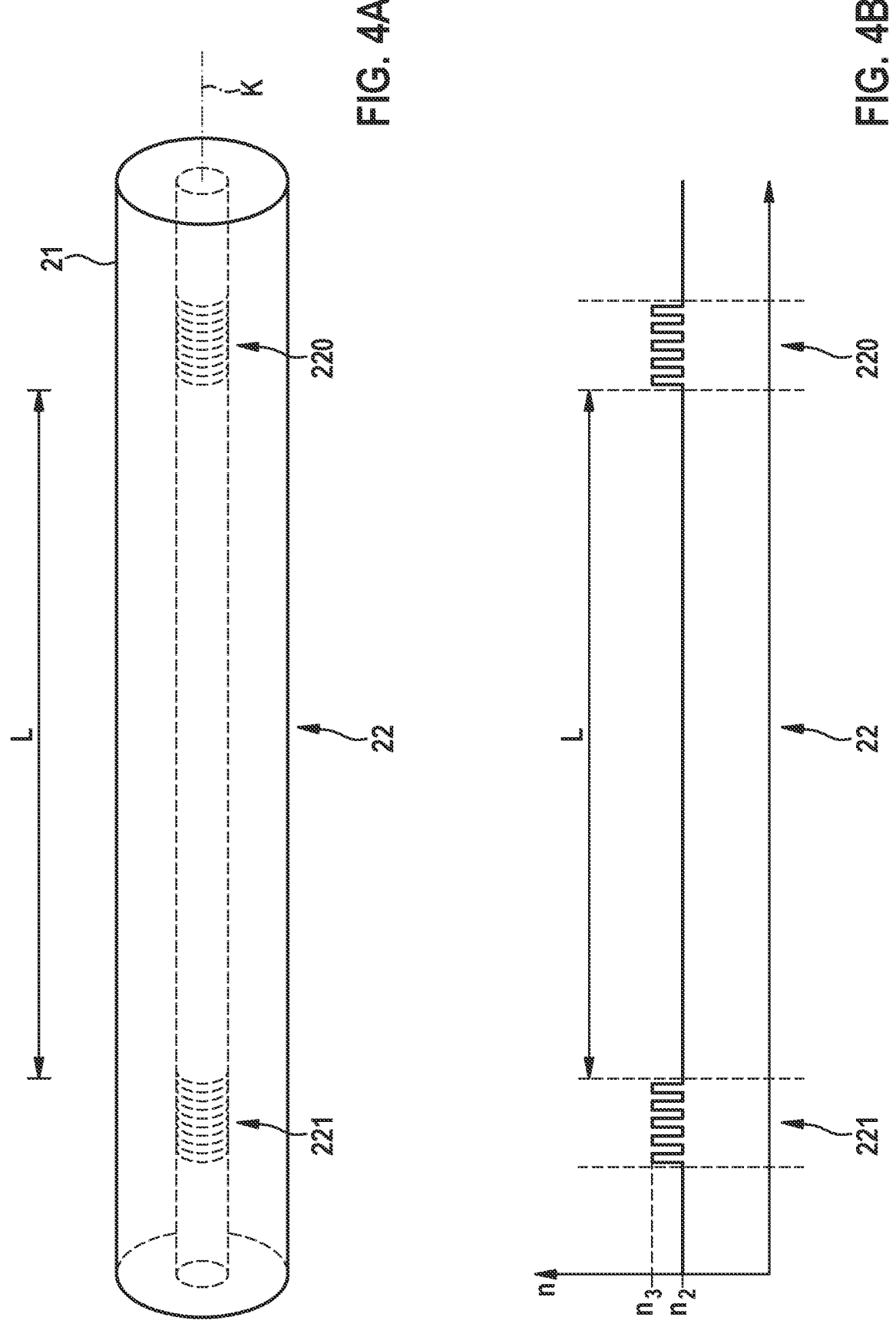
FIG. 4A a schematic view of a sensor device comprising two optical gratings arranged at a distance from one another.
FIG. 4B a view showing a modification of the refractive index of the optical fiber in the region of the optical gratings.

Each sensor device 22, 23, 24 comprises two optical gratings 220, 221, 230, 231, 240, 241 which, as can be seen from FIG. 4A, are arranged at a distance L from one another. The gratings 220, 221, 230, 231, 240, 241 are each formed by a periodic modification of the refractive index n2, n3 of the inner core of the optical fiber 21, as can be seen from FIG. 4B, so that this results in a periodic structure having a periodically varying refractive index n2, n3 in the region of each optical grating 220, 221, 230, 231, 240, 241.

For example, the optical gratings 220, 221, 230, 231, 240, 241 of each sensor device 22, 23, 24 can form a fiber Bragg grating. The gratings 220, 221, 230, 231, 240, 241 can be configured in the same way with the same center wavelength or differently with different center wavelengths.

In one embodiment, the optical gratings 220, 221, 230, 231, 240, 241 of each sensor device 22, 23, 24 each form a fiber Bragg grating having the same center wavelength, so that the optical gratings 220, 221, 230, 231, 240, 241 together form a Fabry-Perot interferometer.

In another embodiment, the optical gratings 220, 221, 230, 231, 240, 241 of each sensor device 22, 23, 24 each form a fiber Bragg grating, wherein the center wavelengths of the optical gratings 220, 221, 230, 231, 240, 241, however, differ from one another.

In yet another embodiment, one of the optical gratings 220, 221, 230, 231, 240, 241 of each sensor device 22, 23, 24 is configured as a fiber Bragg grating and the other of the optical gratings 220, 221, 230, 231, 240, 241 is configured as a long-period grating.

Depending on how the optical gratings 220, 221, 230, 231, 240, 241 are configured, different information can be obtained and evaluated for the measurement of a force effect.

If the optical gratings 220, 221, 230, 231, 240, 241 are configured as fiber Bragg gratings having the same center wavelength, temperature compensation can take place so that the force effect can be determined without the influence of temperature. This is also possible when one of the optical gratings 220, 221, 230, 231, 240, 241 is configured as a fiber Bragg grating and the other of the gratings 220, 221, 230, 231, 240, 241 is configured as a long-period grating.

If the optical gratings 220, 221, 230, 231, 240, 241 are configured as fiber Bragg gratings having different center wavelengths, the information obtained at the gratings 220, 221, 230, 231, 240, 241 of each sensor device 22, 23, 24 are averaged, so that measurement accuracy can be improved in this way.

If one of the optical gratings 220, 221, 230, 231, 240, 241 is configured as a fiber Bragg grating and the other of the optical gratings 220, 221, 230, 231, 240, 241 is configured as a long-period grating, this results in a change in wavelength as a function of an elongation and a change in temperature for each of the gratings 220, 221, 230, 231, 240, 241 using the following equation:

$$\Delta\lambda_b = K_\delta \cdot \Delta\varepsilon + K_T \cdot \Delta T$$

$\Delta\lambda_b$ here writes the change in wavelength in a reflection signal, which is obtained using the respective grating 220, 221, 230, 231, 240, 241 as a function of the change in elongation $\Delta\varepsilon$ and the change in temperature $\Delta T$.

The constant $K_\delta$ is determined by $$K_\delta = (1 - P_e) \cdot \lambda_b^0$$

where $P_e$ is the so-called Pockels coefficient and $$\lambda_b^0$$

indicates the wavelength in the initial state (without elongation load and at the reference temperature).

In contrast, the constant $K_T$ is determined by $$K_T = (\xi + \alpha) \cdot \lambda_b^0$$

where $\xi$ and $\alpha$ indicate the thermo-optic coefficient and the thermal expansion coefficient of the optical fiber 21.

When the optical fiber 21 is elongated in the region of a sensor device 22, 23, 24, there is a shift in the resonant center wavelength of each optical grating 220, 221, 230, 231, 240, 241, wherein the shift for the different gratings 220, 221, 230, 231, 240, 241 of each sensor device 22, 23, 24 is different. This results in a system of equations having two equations and two unknowns (the change in elongation $\Delta\varepsilon$ due to the force effect and the change in temperature $\Delta T$), which can be solved with a view to the change in elongation and the change in temperature, so that a differentiation can be made between the change in elongation and the change in temperature and the change in elongation that is solely due to the force effect can thus be determined while compensating for the temperature influence:

$$\begin{pmatrix} \Delta\lambda_{bL} \\ \Delta\lambda_{bF} \end{pmatrix} = \begin{pmatrix} K_{TL} & K_{\delta L} \\ K_{TF} & K_{\delta F} \end{pmatrix} \cdot \begin{pmatrix} \Delta T \\ \Delta\varepsilon \end{pmatrix}$$

$\Delta\lambda_{bL}$, $K_{TL}$ and $K_{\delta L}$ denote here the change in wavelength and the constants for the long-period grating, while $\Delta\lambda_{bF}$, $K_{TF}$ and $K_{\delta F}$ indicate the change in wavelength and the constants for the fiber Bragg grating.

On the basis of this system of equations and the information about the different wavelength changes and the known constants obtained by means of the different gratings 220, 221, 230, 231, 240, 241, the change in elongation due to the force effect on the force transducer 20 for each sensor device 22, 23, 24 are resolved, so that for each sensor device 22, 23, 24, a value for the force effect for the respective force direction associated with the sensor device 22, 23, 24 can be determined on the basis of a calibration carried out in advance.

Figure 5:
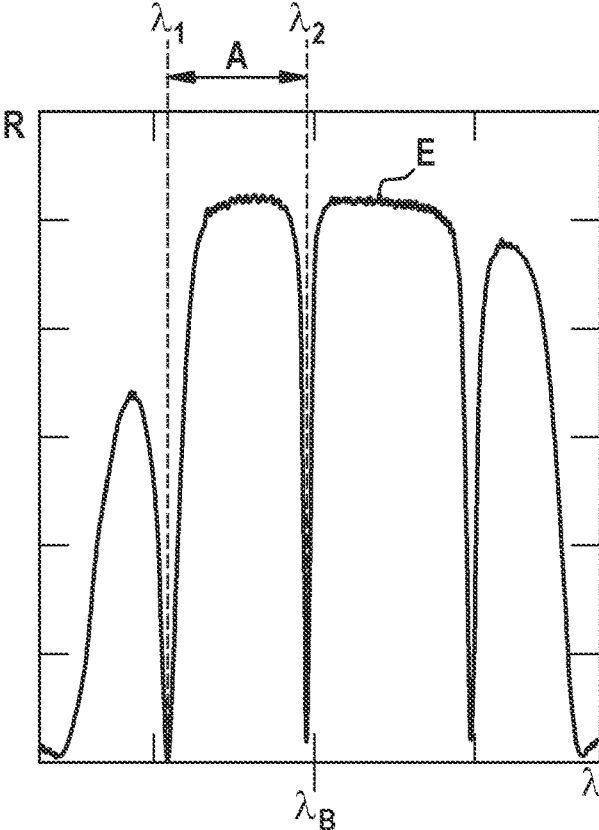
FIG. 5 a view of a spectrum obtained when using a sensor device comprising two optical gratings in the form of fiber Bragg gratings, which together form a Fabry-Perot interferometer.

If the gratings 220, 221, 230, 231, 240, 241 are configured as fiber Bragg gratings having the same center wavelength, then the gratings 220, 221, 230, 231, 240, 241 form a Fabry-Perot interferometer in which a spectrum results in a reflection signal, as shown by way of example in FIG. 5.

An envelope E of the spectrum is determined by the fiber Bragg grating per se, particularly the center wavelength $\lambda_B$ and the width of the envelope E of the spectrum. In the spectrum, there are lines at which the reflection R is essentially zero (for example, at wavelengths $\lambda_1$, $\lambda_2$, which are arranged at a distance A from one another). These lines result from the interaction of the gratings 220, 221, 230, 231, 240, 241 as a Fabry-Perot interferometer, in which a transmission is maximal (and a reflection is therefore minimal) when there is a constructive interference between the signals reflected from the individual gratings 220, 221, 230, 231, 240, 241.

Figure 6:
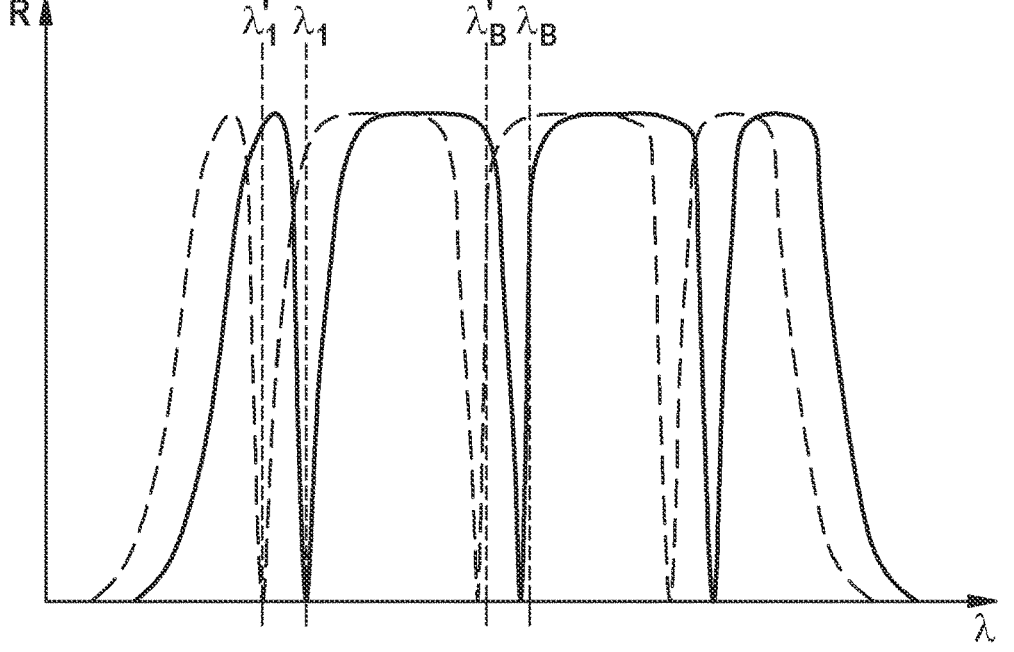
FIG. 6 a schematic view of a change in wavelength on an obtained spectrum.

When there is a change of elongation of the optical fiber 21, the center wavelength $\lambda_B$ of the envelope E shifts, as can be seen from FIG. 6 (center wavelength $\lambda_B'$). In addition, the position of the line structure caused by the Fabry-Perot interferometer also shifts, illustrated by a shift in the wavelength $\lambda_1$ to $\lambda_1'$. From the interaction of the gratings 220, 221, 230, 231, 240, 241 of each sensor device 22, 23, 24, in turn, different information can thus be obtained relating to the shift of the center wavelength $\lambda_B$, the fiber Bragg grating and the shift in the line structure of the Fabry-Perot interferometer. These items of information are different from one another and can be evaluated in order to differentiate a change in elongation due to the force effect and the influence of a change in temperature, using a system of equations that can be specified analogously to the equations described above. The change in elongation due to the force effect can thus be determined while compensating for the temperature influence, so that, in turn, the force effect on the force transducer 20 can be determined with great accuracy.

The evaluation can take place in an evaluation device 3, as is depicted schematically in FIG. 1.

In the embodiment of the force transducer 20 of the measuring device 2 depicted in FIGS. 2 and 3, a force measurement takes place in a plane spanned by the spatial directions X, Y perpendicular to the longitudinal axis K. Additionally or alternatively, a force measurement is however also possible axially along the longitudinal axis K, using transducer sections that can be moved axially with respect to one another.

Figure 7:
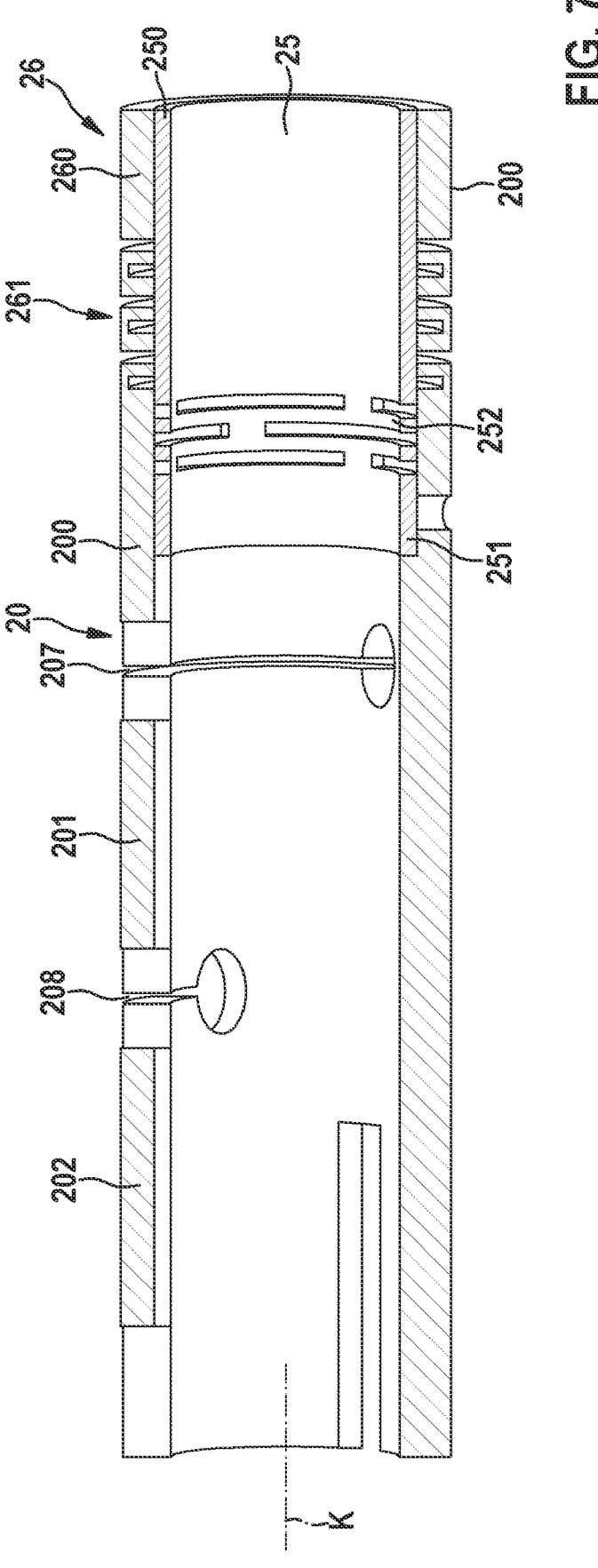
FIG. 7 a view of an embodiment of a force transducer in connection with an inner tubular element.
Figure 8:
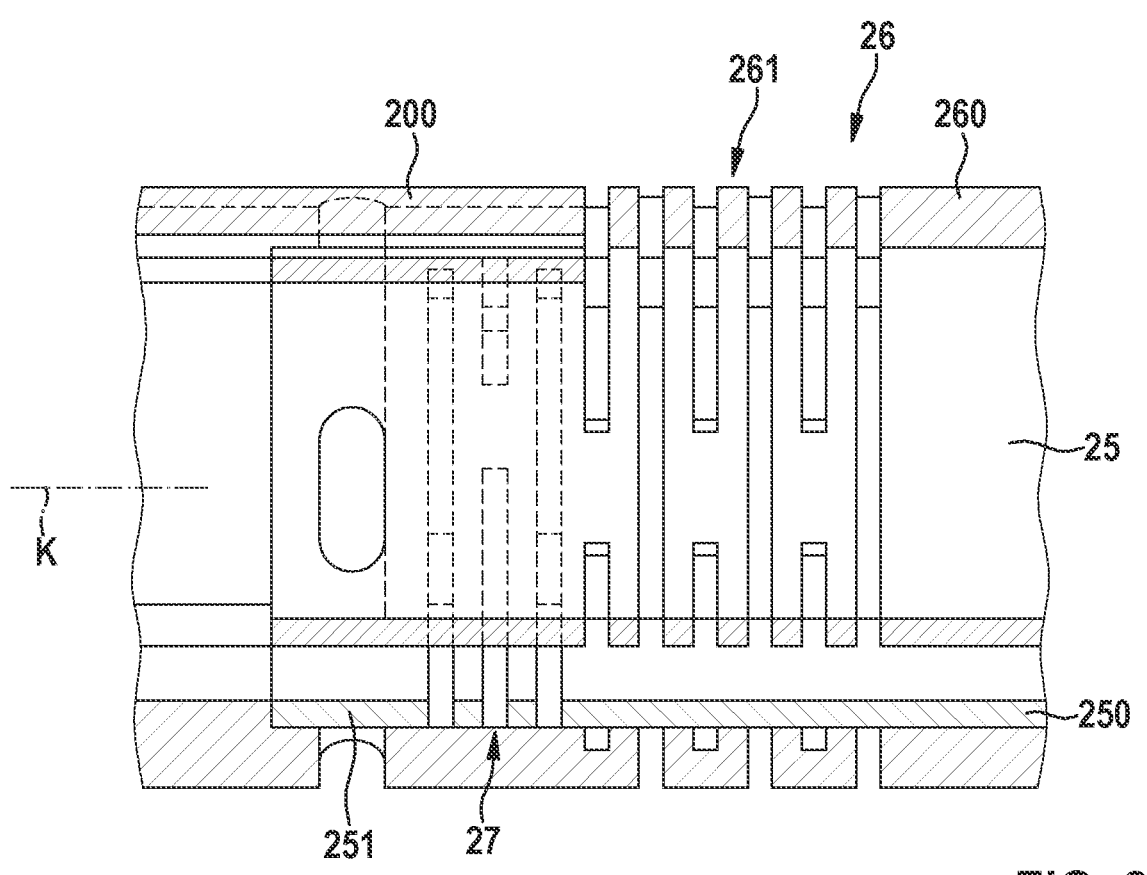
FIG. 8 a view of the inner tubular element in connection with the force transducer.
Figure 9:
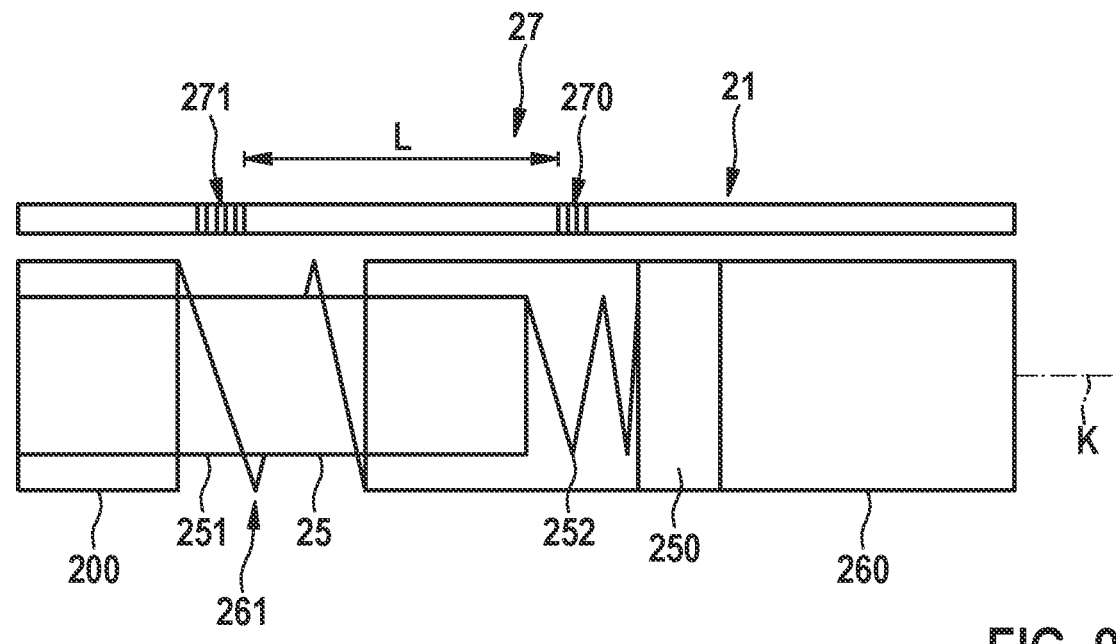
FIG. 9 a schematic functional drawing of the force transducer in connection with the inner tubular element, together with an optical fiber and a sensor device formed thereon.

In an embodiment depicted in FIGS. 7 to 9, a force transducer 20 is arranged on an inner tubular element 25 and is connected, for example, to the body 10 of the catheter device 1 (see FIG. 1) by means of the inner tubular element 25.

In the embodiment depicted, transducer sections 200, 260 are connected to one another in the region of an end 26 of the force transducer 20 by means of a connecting section 261 in the form of an axially resilient spring section formed by recesses in the force transducer 20 in such a way that transducer sections 200, 260 are axially movable with respect to one another along longitudinal axis K. A sensor device 27 (see FIG. 9), which is arranged in the region of the transducer sections 200, 260, can thus determine an axial change in length and thus a force effect in the axial direction. Alternatively, the connecting section 261 in the form of an axially resilient spring section formed by recesses in the force transducer 20 can also be arranged in the center of the force transducer 20, for example, in the transducer section 201 or at the other end, for example, in the transducer section 202.

In the depicted embodiment, the inner tubular element 25 comprises support sections 250, 251, of which a first support section 250 is fixedly connected to the transducer section 260, for example, welded, and of which a second support section 251 is fixedly connected to the transducer section 200, for example, welded. A spring section 252, which is axially resilient and thus enables an axial, elastic movement of the support sections 250, 251 with respect to one another, is arranged between the support sections 250, 251.

The spring sections of the inner tubular element and the spring sections of the transducer are preferably offset from one another along the longitudinal axis in such a way that a transducer section stabilizes the spring section of the inner tube against bending and a section of the inner tube stabilizes the spring section of the force transducer. This increases the overall stability against bending.

In the depicted embodiment, both the transducer sections 200, 260 and the support sections 250, 251, which are fixedly connected to the transducer sections 200, 260, can thus be moved axially with respect to one another. The result is a parallel connection of spring sections 252, 261, as depicted schematically in FIG. 9, which enables the transducer sections 200, 260 to move axially with respect to one another, with an arrangement of the force transducer 20 on the inner tubular element 25 that is insensitive to tolerances.

An optical fiber 21 having two optical gratings 270, 271 can also be arranged on the force transducer 20 depicted in FIGS. 7 to 9. The optical gratings 270, 271 are preferably arranged on the force transducer 21 in such a way that the connecting section 261 is arranged between the optical gratings 270, 271 in the form of an axially resilient spring section formed by recesses in the force transducer 20. Said optical gratings 270, 271 can also be configured as fiber Bragg gratings having the same center wavelength and thus together form a Fabry-Perot interferometer, or configured as fiber Bragg gratings having different center wavelengths. One of the optical gratings 270, 271 of each sensor device 22, 23, 24 can also be configured as a fiber Bragg grating and the other of the optical gratings 270, 271 as a long-period grating.

The idea on which the present invention is based is not restricted to the embodiments described above, but can in principle also be implemented differently.

A force transducer of the measuring device can comprise two or more transducer sections which can be moved with respect to one another transversely to the longitudinal axis or along the longitudinal axis. A sensor device can be arranged on each pair of transducer sections, wherein each sensor device comprises two optical gratings for determining a force effect on a respective pair of transducer sections.

A catheter device can be designed as an ablation catheter, for example. A catheter device of the type described here can, however, also be implemented for a different purpose and is therefore not limited to use as an ablation catheter.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE SYMBOLS

1 Catheter device
10 Body
11 Electrode
12 Proximal end
2 Measuring device
20 Force transducer
200-203 Transducer section
204-206 Connecting section
207-209 Recess
21 Fiber
22 Sensor device
220, 221 Optical grating
23 Sensor device
230, 231 Optical grating
24 Sensor device
240, 241 Optical grating
25 Inner tubular element
250, 251 Support section
252 Spring section
26 Connection end
260 Transducer section
261 Connecting section (spring section)
27 Sensor device
270, 271 Optical grating
3 Evaluation device
A Distance
E Envelope
G Tissue
K Longitudinal axis L Distance $\lambda_1$, $\lambda_1'$, $\lambda_2$ Wavelength $\lambda_B$, $\lambda_B'$ Center wavelength of the Bragg grating R Reflectivity X, Y, Z Spatial direction

The invention claimed is:

1. A catheter device, comprising a measuring device for measuring a force effect on the catheter device, the measuring device comprising a force transducer comprising a plurality of transducer sections and an optical fiber arranged on the force transducer, the transducer sections forming at least one pair of adjacent transducer sections connected to one another by means of a connecting section and, with deformation of the connecting section, are movable with respect to one another and the optical fiber comprising at least one sensor device for measuring a force effect between the transducer sections of the at least one pair of adjacent transducer sections, wherein the at least one sensor device comprises a first optical grating and a second optical grating for measuring a force effect between the transducer sections of the at least one pair of adjacent transducer sections.

2. The catheter device according to claim 1, wherein the plurality of transducer sections are lined up along a longitudinal axis, wherein the optical fiber particularly extends along the longitudinal axis.

3. The catheter device according to claim 2, wherein that the connecting section of at least one pair of adjacent transducer sections can be bent about a defined spatial direction extending transversely to the longitudinal axis in such a way that the transducer sections of the at least one pair of adjacent transducer sections can be moved about the defined spatial direction with respect to one another by means of the connecting section.

4. The catheter device according to claim 2, wherein the force transducer forms at least two pairs of adjacent transducer sections which are each connected to one another by means of a connecting section and can be moved with respect to one another about different spatial directions extending transversely to the longitudinal axis, wherein the optical fiber comprises at least two sensor devices each comprising two optical gratings which are each associated with a pair of adjacent transducer sections for measuring a force effect between the adjacent transducer sections.

5. The catheter device according to claim 2, wherein the connecting section of at least one pair of adjacent transducer sections is deformable axially along the longitudinal axis in such a way that the transducer sections of the at least one pair of adjacent transducer sections can be moved with respect to one another axially along the longitudinal axis by means of the connecting section.

6. The catheter device according to claim 5, wherein the connecting section is formed by an axially resilient spring section.

7. The catheter device according to claim 5, wherein an inner tubular element which is arranged radially inside the force transducer and which comprises a first support section connected to a transducer section of the at least one pair of adjacent transducer sections and a second support section connected to the other transducer section of the at least one pair of adjacent transducer sections, wherein the first support section and the second support section are connected to one another by means of an axially resilient spring section.

8. The catheter device according to claim 2, wherein the first optical grating and the second optical grating are spaced from one another by a distance along the longitudinal axis.

9. The catheter device according to claim 1, wherein the first optical grating and the second optical grating are each configured as a fiber Bragg grating.

10. The catheter device according to claim 1, wherein one of the first optical grating and the second optical grating is configured as a fiber Bragg grating and the other of the first optical grating and the second optical grating is configured as a long-period grating.

11. The catheter device according to claim 1, wherein the first optical grating and the second optical grating together form a Fabry-Perot interferometer.

12. The catheter device according to claim 1, wherein an evaluation device which is configured to evaluate an optical signal obtained on the basis of an optical signal fed into the optical fiber of the measuring device, in order to determine a force effect on the force transducer.

13. The catheter device according to claim 12, wherein optical signals from different sensor devices differ in wavelength.

14. The catheter device according to claim 12, wherein the evaluation device is configured to evaluate a change in wavelength of the optical signal to determine the force effect and thereby to take into account an influence of a change in temperature on the change in wavelength to compensate for the change in temperature when determining the force effect.

* * * * *